(12) United States Patent
Kapre et al.

(10) Patent No.: US 10,076,563 B2
(45) Date of Patent: Sep. 18, 2018

(54) *BORDETELLA PERTUSSIS* IMMUNOGENIC VACCINE COMPOSITIONS

(71) Applicant: Inventprise, LLC, Bellevue, WA (US)

(72) Inventors: Subhash V. Kapre, Redmond, WA (US); Francis Michon, Bethesda, MD (US)

(73) Assignee: Inventprise, LLC, Redmond, WA (US)

( * ) Notice: Subject to any disclaimer, the term of this patent is extended or adjusted under 35 U.S.C. 154(b) by 0 days.

(21) Appl. No.: 15/131,674

(22) Filed: Apr. 18, 2016

(65) Prior Publication Data

US 2016/0303216 A1 Oct. 20, 2016

Related U.S. Application Data

(60) Provisional application No. 62/148,529, filed on Apr. 16, 2015.

(51) Int. Cl.
*A61K 39/00* (2006.01)
*A61K 39/02* (2006.01)
*A61K 39/39* (2006.01)

(52) U.S. Cl.
CPC ............ *A61K 39/099* (2013.01); *A61K 39/39* (2013.01); *A61K 2039/55516* (2013.01); *A61K 2039/575* (2013.01); *A61K 2039/58* (2013.01); *A61K 2039/6031* (2013.01); *A61K 2039/6037* (2013.01); *A61K 2039/6068* (2013.01); *A61K 2039/6087* (2013.01); *A61K 2039/627* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 8,097,437 B2 | 1/2012 | Kapre et al. | |
| 8,398,985 B2 | 3/2013 | Kapre et al. | |
| 9,102,741 B2 * | 8/2015 | Margarit Y Ros ... | A61K 39/092 |
| 9,283,270 B2 * | 3/2016 | Kapre .................. | A61K 39/385 |
| 9,452,213 B2 * | 9/2016 | Kapre .................. | A61K 39/39 |
| 9,528,086 B2 * | 12/2016 | Locht .................. | A61K 39/092 |
| 9,957,485 B2 * | 5/2018 | Kapre .................... | C12N 7/00 |
| 2007/0116711 A1 | 5/2007 | Castado | |
| 2010/0086974 A1 | 4/2010 | Kapre et al. | |
| 2010/0092519 A1 | 4/2010 | Kapre et al. | |
| 2010/0129881 A1 | 5/2010 | Kapre et al. | |
| 2013/0209503 A1 * | 8/2013 | Kapre .................. | A61K 39/385 424/195.11 |
| 2015/0017209 A1 | 1/2015 | Pichichero | |
| 2015/0056250 A1 | 2/2015 | Kapre | |
| 2015/0064768 A1 | 3/2015 | Kapre | |
| 2015/0147780 A1 * | 5/2015 | Dinescu ................. | C12P 23/00 435/67 |
| 2015/0344530 A1 | 12/2015 | Kapre | |
| 2016/0015806 A1 * | 1/2016 | Kapre .................... | A61K 39/39 424/190.1 |
| 2016/0303216 A1 * | 10/2016 | Kapre .................. | A61K 39/099 |
| 2017/0000882 A1 * | 1/2017 | Kapre .................... | A61K 39/39 |
| 2017/0065704 A1 * | 3/2017 | Kapre ...................... | A61K 9/19 |
| 2017/0072043 A1 * | 3/2017 | Kapre .................. | A61K 39/092 |
| 2018/0071380 A1 * | 3/2018 | Makidon ............... | A61K 39/099 |

FOREIGN PATENT DOCUMENTS

| | | | |
|---|---|---|---|
| WO | WO 2009/004102 A2 * | 1/2009 | |
| WO | WO 2016/011155 A1 * | 1/2016 | |
| WO | WO 2016/168815 A1 * | 10/2016 | |
| WO | WO-2016168815 A1 * | 10/2016 | ........... A61K 39/099 |

OTHER PUBLICATIONS

Sharma et al, Vaccine, 2012, 30:6157-6162; available online Aug. 5, 2012.*
PCT Search and Patentability Report for PCT/US2016/028093, dated Aug. 18, 2016.
AU Examination Report No. 1 for Application No. 2016/248452 dated Apr. 1, 2018.

* cited by examiner

*Primary Examiner* — Nita M. Minnifield
(74) *Attorney, Agent, or Firm* — Remenick PLLC (57) ABSTRACT

This invention is directed to composition, vaccines, tools and methods in the treatment and prevention of *Bordetella pertussis*. In particular, the invention is directed to a three-pronged approach that involves removal of the nonessential vaccine components, use of a nondenatured, genetically detoxified mutant, and adding virulence factors.

23 Claims, 2 Drawing Sheets
Specification includes a Sequence Listing.

Figure 1

```
SEQ ID NO1

MQQSHQAGYANAADRESGIPAAVLDGIKAVAKEKNATLMFRLVNPHSTSLIAEGVATMGL

GVHAKSSDWGLQAGYIPVNPNLSKLFGRAPEVIARADNDVNSSLAHGHTAVDLTLSKERL

DYLRQAGLVTGMADGVVASNHAGYEQFEFRVKETSDGRYAVQYRRKGGDDFEAVKVIGNA

AGIPLTADIDMFAIMPHLSNFRDSARSSVTSGDSVTDYLARTRRAASEATGGLDRERIDL

LWKIARAGARSAVGTEARRQFRYDGDMNIGVITDFELEVRNALNRRAHAVGAQDVVQHGT

EQNNPFPEADEKIFVVSATGESQMLTRGQLKEYIGQQRGEGYVFYENRAYGVAGKSLFDD

GLGAAPGVPSGRSKFSPDVLETVPASPGLRRPSLGAVERQDSGYDSLDGVGSRSFSLGEV

SDMAAVEAAELEMTRQVLHAGARQDDAEPGVSGASAHWGQRALQGAQAVVLDVAAGGIDI

ASRKGERPALTFITPLAAPGEEQRRRTKTGKSEFTTFVEIVGKQDRWRIRDGAADTTIDL

AKVVSQLVDANGVLKHSIKLDVIGGDGDDVVLANASRIHYDGGAGTNTVSYAALGRQDSI

TVSADGERFNVRKQLNNANVYREGVATQTTAYGKRTENVQYRHVELARVGQLVEVDTLEH

VQHIIGGAGNDSITGNAHDNFLAGGSGDDRLDGGAGNDTLVGGEGQNTVIGGAGDDVFLQ

DLGVWSNQLDGGAGVDTVKYNVHQPSEERLERMGDTGIHADLQKGTVEKWPALNLFSVDH

VKNIENLHGSRLNDRIAGDDQDNELWGHDGNDTIRGRGGDDILRGGLGLDTLYGEDGNDI

FLQDDETVSDDIDGGAGLDTVDYSAMIHPGRIVAPHEYGFGIEADLSREWVRKASALGVD

YYDNVRNVENVIGTSMKDVLIGDAKANTLMGQGGDDTVRGGDGDDLLFGGDGNDMLYGDA

GNDTLYGGLGDDTLEGGAGNDWFGQTQAREHDVLRGGDGVDTVDYSQTGAHAGIAAGRIG

LGILADLGAGRVDKLGEAGSSAYDTVSGIENVVGTELADRITGDAQANVLRGAGGADVLA

GGEGDDVLLGGDGDDQLSGDAGRDRLYGEAGDDWFFQDAANAGNLLDGGDGRDTVDFSGP

GRGLDAGAKGVFLSLGKGFASLMDEPETSNVLRNIENAVGSARDDVLIGDAGANVLNGLA

GNDVLSGGAGDDVLLGDEGSDLLSGDAGNDDLFGGQGDDTYLFGVGYHDTIYESGGGHD

TIRINAGADQLWFARQGNDLEIRILGTDDALTVHDWYRDADHRVEIIHAANQAVDQAGIE

KLVEAMAQYPDPGAAAAAPPAARVPDTLMQSLAVNWR
```

Figure 2

Formula 1

Formula 2

α-GlcNAc-4-β-ManNAc3NAcA-3-β-FucNAc4NMe-linker-R

R= -CH=O; -COOH;-CH2-SH

Formula 3

SEQUENCE LISTING

```
<160> NUMBER OF SEQ ID NOS: 1

<210> SEQ ID NO 1
<211> LENGTH: 1357
<212> TYPE: PRT
<213> ORGANISM: Bordetella pertussis

<400> SEQUENCE: 1

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Met Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110
```

-continued

Leu Thr Leu Ser Lys Glu Arg Leu Asp Tyr Leu Arg Gln Ala Gly Leu
            115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser Ala His Trp Gly Gln Arg Ala Leu Gln
    450                 455                 460

Gly Ala Gln Ala Val Val Leu Asp Val Ala Ala Gly Gly Ile Asp Ile
465                 470                 475                 480

Ala Ser Arg Lys Gly Glu Arg Pro Ala Leu Thr Phe Ile Thr Pro Leu
                485                 490                 495

Ala Ala Pro Gly Glu Glu Gln Arg Arg Thr Lys Thr Gly Lys Ser
            500                 505                 510

Glu Phe Thr Thr Phe Val Glu Ile Val Gly Lys Gln Asp Arg Trp Arg
        515                 520                 525

Ile Arg Asp Gly Ala Ala Asp Thr Thr Ile Asp Leu Ala Lys Val Val

-continued

```
            530                 535                 540
Ser Gln Leu Val Asp Ala Asn Gly Val Leu Lys His Ser Ile Lys Leu
545                 550                 555                 560

Asp Val Ile Gly Gly Asp Gly Asp Val Val Leu Ala Asn Ala Ser
                    565                 570                 575

Arg Ile His Tyr Asp Gly Gly Ala Gly Thr Asn Thr Val Ser Tyr Ala
                580                 585                 590

Ala Leu Gly Arg Gln Asp Ser Ile Thr Val Ser Ala Asp Gly Glu Arg
                595                 600                 605

Phe Asn Val Arg Lys Gln Leu Asn Asn Ala Asn Val Tyr Arg Glu Gly
                610                 615                 620

Val Ala Thr Gln Thr Thr Ala Tyr Gly Lys Arg Thr Glu Asn Val Gln
625                 630                 635                 640

Tyr Arg His Val Glu Leu Ala Arg Val Gly Gln Leu Val Glu Val Asp
                645                 650                 655

Thr Leu Glu His Val Gln His Ile Ile Gly Ala Gly Asn Asp Ser
                660                 665                 670

Ile Thr Gly Asn Ala His Asp Asn Phe Leu Ala Gly Gly Ser Gly Asp
                675                 680                 685

Asp Arg Leu Asp Gly Gly Ala Gly Asn Asp Thr Leu Val Gly Gly Glu
                690                 695                 700

Gly Gln Asn Thr Val Ile Gly Gly Ala Gly Asp Asp Val Phe Leu Gln
705                 710                 715                 720

Asp Leu Gly Val Trp Ser Asn Gln Leu Asp Gly Gly Ala Gly Val Asp
                725                 730                 735

Thr Val Lys Tyr Asn Val His Gln Pro Ser Glu Glu Arg Leu Glu Arg
                740                 745                 750

Met Gly Asp Thr Gly Ile His Ala Asp Leu Gln Lys Gly Thr Val Glu
                755                 760                 765

Lys Trp Pro Ala Leu Asn Leu Phe Ser Val Asp His Val Lys Asn Ile
770                 775                 780

Glu Asn Leu His Gly Ser Arg Leu Asn Asp Arg Ile Ala Gly Asp Asp
785                 790                 795                 800

Gln Asp Asn Glu Leu Trp Gly His Asp Gly Asn Asp Thr Ile Arg Gly
                805                 810                 815

Arg Gly Gly Asp Asp Ile Leu Arg Gly Gly Leu Gly Leu Asp Thr Leu
                820                 825                 830

Tyr Gly Glu Asp Gly Asn Asp Ile Phe Leu Gln Asp Asp Glu Thr Val
                835                 840                 845

Ser Asp Asp Ile Asp Gly Gly Ala Gly Leu Asp Thr Val Asp Tyr Ser
850                 855                 860

Ala Met Ile His Pro Gly Arg Ile Val Ala Pro His Glu Tyr Gly Phe
865                 870                 875                 880

Gly Ile Glu Ala Asp Leu Ser Arg Glu Trp Val Arg Lys Ala Ser Ala
                885                 890                 895

Leu Gly Val Asp Tyr Tyr Asp Asn Val Arg Asn Val Glu Asn Val Ile
                900                 905                 910

Gly Thr Ser Met Lys Asp Val Leu Ile Gly Asp Ala Lys Ala Asn Thr
                915                 920                 925

Leu Met Gly Gln Gly Gly Asp Asp Thr Val Arg Gly Gly Asp Gly Asp
930                 935                 940

Asp Leu Leu Phe Gly Gly Asp Gly Asn Asp Met Leu Tyr Gly Asp Ala
945                 950                 955                 960
```

-continued

```
Gly Asn Asp Thr Leu Tyr Gly Gly Leu Gly Asp Asp Thr Leu Glu Gly
            965                 970                 975
Gly Ala Gly Asn Asp Trp Phe Gly Gln Thr Gln Ala Arg Glu His Asp
            980                 985                 990
Val Leu Arg Gly Gly Asp Gly Val Asp Thr Val Asp Tyr Ser Gln Thr
            995                 1000                1005
Gly Ala His Ala Gly Ile Ala Ala Gly Arg Ile Gly Leu Gly Ile
        1010            1015            1020
Leu Ala Asp Leu Gly Ala Gly Arg Val Asp Lys Leu Gly Glu Ala
        1025            1030            1035
Gly Ser Ser Ala Tyr Asp Thr Val Ser Gly Ile Glu Asn Val Val
        1040            1045            1050
Gly Thr Glu Leu Ala Asp Arg Ile Thr Gly Asp Ala Gln Ala Asn
        1055            1060            1065
Val Leu Arg Gly Ala Gly Gly Ala Asp Val Leu Ala Gly Gly Glu
        1070            1075            1080
Gly Asp Asp Val Leu Leu Gly Gly Asp Gly Asp Asp Gln Leu Ser
        1085            1090            1095
Gly Asp Ala Gly Arg Asp Arg Leu Tyr Gly Glu Ala Gly Asp Asp
        1100            1105            1110
Trp Phe Phe Gln Asp Ala Ala Asn Ala Gly Asn Leu Leu Asp Gly
        1115            1120            1125
Gly Asp Gly Arg Asp Thr Val Asp Phe Ser Gly Pro Gly Arg Gly
        1130            1135            1140
Leu Asp Ala Gly Ala Lys Gly Val Phe Leu Ser Leu Gly Lys Gly
        1145            1150            1155
Phe Ala Ser Leu Met Asp Glu Pro Glu Thr Ser Asn Val Leu Arg
        1160            1165            1170
Asn Ile Glu Asn Ala Val Gly Ser Ala Arg Asp Val Leu Ile
        1175            1180            1185
Gly Asp Ala Gly Ala Asn Val Leu Asn Gly Leu Ala Gly Asn Asp
        1190            1195            1200
Val Leu Ser Gly Gly Ala Gly Asp Asp Val Leu Leu Gly Asp Glu
        1205            1210            1215
Gly Ser Asp Leu Leu Ser Gly Asp Ala Gly Asn Asp Asp Leu Phe
        1220            1225            1230
Gly Gly Gln Gly Asp Asp Thr Tyr Leu Phe Gly Val Gly Tyr Gly
        1235            1240            1245
His Asp Thr Ile Tyr Glu Ser Gly Gly Gly His Asp Thr Ile Arg
        1250            1255            1260
Ile Asn Ala Gly Ala Asp Gln Leu Trp Phe Ala Arg Gln Gly Asn
        1265            1270            1275
Asp Leu Glu Ile Arg Ile Leu Gly Thr Asp Asp Ala Leu Thr Val
        1280            1285            1290
His Asp Trp Tyr Arg Asp Ala Asp His Arg Val Glu Ile Ile His
        1295            1300            1305
Ala Ala Asn Gln Ala Val Asp Gln Ala Gly Ile Glu Lys Leu Val
        1310            1315            1320
Glu Ala Met Ala Gln Tyr Pro Asp Pro Gly Ala Ala Ala Ala Ala
        1325            1330            1335
Pro Pro Ala Ala Arg Val Pro Asp Thr Leu Met Gln Ser Leu Ala
        1340            1345            1350
```

```
Val Asn Trp Arg
   1355
```

BORDETELLA PERTUSSIS IMMUNOGENIC VACCINE COMPOSITIONS

REFERENCE TO RELATED APPLICATIONS

This application claims priority to U.S. Provisional Application No. 62/148,529 filed Apr. 16, 2015, which is specifically and entirely incorporated by reference.

SEQUENCE LISTING

The instant application contains a Sequence Listing which has been submitted electronically in ASCII format and is hereby incorporated by reference in its entirety. Said ASCII copy, created on May 10, 2016, is named 3036.010.US_S-L.txt and is 12,050 bytes in size.

1. FIELD OF THE INVENTION

This invention is directed to composition, vaccines, tools and methods in the treatment and prevention of *Bordetella pertussis*. In particular, the invention is directed to a three-pronged approach that involves removal of the nonessential vaccine components, use of a nondenatured, genetically detoxified mutant, and adding virulence factors.

2. BACKGROUND OF THE INVENTION

Introduction of whole-cell pertussis (wP) vaccines in the late 1940s resulted in a rapid reduction in both the incidence of pertussis and death caused by the infection. However, the success of these vaccines was undermined by concerns over safety issues. Thus, they were replaced with acellular pertussis (aP) vaccines in the late 1990s in many developed countries (1). Since then, pertussis cases have increased and dramatic epidemic cycles have returned. In 2012, 48,277 cases of pertussis and 18 deaths were reported to the Centers for Disease Control and Prevention (CDC), which represents the greatest burden of pertussis in the United States in 60 years and similar outbreaks are occurring in other countries (2-4). However, the epidemiology of contemporary pertussis does not replicate that of the pre-vaccine era. Disease is now more common in infants and older children (ages 9 to 19) and, strikingly, these older children are often fully vaccinated according to current recommendations yet develop pertussis (5, 6). Ominously, studies that have analyzed pertussis incidence among children that were born and vaccinated during the transition to aP vaccines have found that the rate of infection is significantly higher among children vaccinated with only aP vaccines compared to those vaccinated with even a single dose of wP vaccine (7). To combat the rise of infections in this group, regulatory agencies have called for boosters to be administered earlier (8). The benefit of boosting with aP vaccines is at best unclear because it is unknown whether the re-emergence of pertussis is due simply to waning immunity or to fundamental differences in the nature of the immune response induced by aP vaccines compared with wP vaccines or with natural infection.

The increased incidence of disease among older children and also adults is especially worrisome because of the corresponding risk of transmission to non- or incompletely-immunized infants (9). Compounding the problem, antibiotic treatment has minimal efficacy by the time most diagnoses are made and severe cases can be unresponsive to standard therapies for respiratory distress, such as mechanical ventilation (10). This re-emergence of pertussis as a global public health problem presents many challenges. For example, needed are vaccines that have an acceptable safety profile, provide long-lasting immunity, reduce infection burden and prevent transmission. Also needed are therapeutic agents and treatment strategies that reduce morbidity and mortality in vulnerable populations (11). Clearly, a strong need exists for improved pertussis vaccines.

SUMMARY OF THE INVENTION

The present invention overcomes the problems and disadvantages associated with current strategies and designs and provides new tools, compositions and methods for the treatment and prevention in infection by *Bordetella pertussis* and related organisms.

One embodiment of the invention is directed to an immunogenic *B. pertussis* vaccine composition comprising a genetically detoxified pertussis toxin (PT); a genetically detoxified pertussis adenylate cyclase toxin (ACT); an immunogenic oligosaccharide or fragment thereof derived from the lipooligosaccharide of *B. pertussis* having one or more of the antigenic determinants of the endotoxin to a carrier protein or peptide; a TLR agonist to induce a protective cell-mediated response against *B. pertussis* wherein when provided to a mammal said composition: produces neutralizing anti toxin antibodies against *B. pertussis*; produces direct bactericidal antibodies against *B. pertussis*; elicits a pertussis toxin-specific Th1/Th17 cell response; generates IFN-δ and IL-17 cytokines wherein said cytokines permit recruitment of neutrophils; and reduces nasopharyngeal colonization and carriage of *B. pertussis* in the vaccine recipient. Preferably the genetically detoxified pertussis toxin is produced in *E. coli*. Also preferably genetically detoxified mutants of pertussis toxin are produced in *B. pertussis*. Preferably the genetically detoxified AC toxin has the primary amino acid SEQ ID NO 1. Preferably the vaccine of the invention induces the production of anti-PT and anti-ACT neutralizing and bactericidal antibodies against *B. pertussis*.

Another embodiment of the invention is directed to an oligosaccharide conjugate comprising a genetically detoxified pertussis toxin (PT); a genetically detoxified pertussis adenylate cyclase toxin (ACT); an immunogenic oligosaccharide or fragment thereof derived from the lipooligosaccharide of *B. pertussis* having one or more of the antigenic determinants of the endotoxin to a carrier protein or peptide; a TLR agonist to induce a protective cell-mediated response against *B. pertussis*. Preferably the oligosaccharide comprises one or more of the oligosaccharides of Formula 1, Formula 2 or Formula 3 of FIG. 2. Also preferably, the pentasaccharide of Formula 3 is synthetic or is a deamination product of the *B. pertussis* LOS. Preferably the oligosaccharide comprises a *B. pertussis* LOS-derived oligosaccharide (OS) or its fragment and the *B. pertussis* derived detoxified toxin (dPT), and the oligosaccharide comprises a *B. pertussis* LOS-derived oligosaccharide (OS) or its fragment and the pertussis derived detoxified toxin (dACT). Preferably the TLR agonist is a TLR-2, a TLR-4 or a TLR-8.

Another embodiment of the invention is directed to methods of immunizing a mammal with the vaccine of claim 1 to prevent disease caused by *B. pertussis*.

Another embodiment of the invention is directed to methods of immunizing a mammal with the vaccine of claim 1 to reduce nasopharyngeal colonization and carriage by *B. pertussis*.

Other embodiments and advantages of the invention are set forth in part in the description, which follows, and in part, may be obvious from this description, or may be learned from the practice of the invention.

DESCRIPTION OF THE DRAWINGS

FIG. 2 depicts the structure of the dodecasaccharide core of B. b characterization of novel TLR2-activating lipoproteins from *B. pertussis* (24). These proteins contain a characteristic N-terminal signal peptide that is unique to Gram negative bacteria and we demonstrate that one of these lipoproteins, BP1569 activates murine dendritic cells and macrophages and human mononuclear cells via TLR2. A corresponding synthetic lipopeptide LP1569 with potent immunostimulatory and adjuvant properties was able to enhance Th1, Th17 and IgG2a antibody responses induced in mice with an experimental Pa, and conferred superior protection against *B. pertussis* infection than an equivalent vaccine formulated with alum (24).

Analysis of T cell responses in children demonstrated that Pa promote Th2-type responses, whereas Pw preferentially induce Th1 cells (25,26). It has also been reported that the superior long term protection induced by wP in mice, when antibody responses had waned significantly, was associated with the induction of potent Th1 responses (27). More recently it has been reported that Th17 cells also play a role in protection induced by natural infection or immunization with wP (28-31).

Genetically detoxified pertussis toxin (dPT) can be obtained and mutants of pertussis toxin suitable for vaccine development can be obtained (43,44a, 44b). dPT-induced Th17 expansion is counter regulated by the PI3K pathway. For its properties and being already used in humans as vaccine Ag in pertussis, dPT may represents a valid candidate adjuvant to foster immune protective response in vaccines against infectious diseases where Th1/Th17 are mediating host immunity (45). As an example, pertussis toxin mutants, *Bordetella* strains capable of producing such mutants and their use in the development of antipertussis vaccines are described in U.S. Pat. No. 7,666,436. Pertussis toxin (PT) mutants are described being immunologically active and having reduced or no toxicity, characterized in that at least one of the amino acid residues Glu129, Asp11, Trp26, Arg9, Phe50, Asp1, Arg13, Tyr130, Gly86, Ile88, Tyr89, Tyr8, Gly44, Thr53 and Gly80 of subunit Si amino acid sequence is deleted and substituted by a different amino acid residue selected in the group of natural amino acids.

*Bordetella* strains capable of providing and secreting said PT mutants and means and methods for obtaining them are also described. The *Bordetella* strains and the PT mutants produced by them are particularly suitable for the preparation of effective cellular and acellular antipertussis vaccines.

Adenylate cyclase toxin is another important virulence factor secreted by *B. pertussis* (and also by other closely related *Bordetella* species). It is an immunogenic protein and can elicit a protective immune response, but it has not been included as a component of acellular pertussis vaccines. ACT consists of an amino terminal adenylate cyclase (AC) domain of approximately 400 amino acids and a pore-forming repeat in toxin (RTX) hemolysin domain of approximately 1300 amino acids with significant homology to *E. coli* hemolysin. ACT is secreted from *B. pertussis* by a type I secretion 'channel-tunnel' mechanism formed by the CyaBDE proteins, and is then modified by fatty acylation on two specific lysine residues in the hemolysin domain mediated by the CyaC acyltransferase (35). Studies in mouse models established ACT as an important virulence factor for *B. pertussis* infection (36-38). A point mutant of *B. pertussis* with abolished AC catalytic activity was greater than 1000 times less pathogenic to newborn mice than wild-type bacteria, directly demonstrating the importance of the AC toxin in pertussis virulence. Similarly, an in-frame deletion mutant of *B. pertussis* that lacks HLY is equally avirulent, supporting observations that the HLY domain plays a critical role in AC toxin entry into cells. Furthermore, the genetically inactivated AC toxin produced by the point mutant is antigenically similar to the native toxin. This strain may be useful in the development of pertussis component vaccines (37). Using PT and ACT deficient mutants it is proposed that PT acts earlier to inhibit neutrophil influx and ACT acts later to intoxicate neutrophils (and other recruited cells) once present at the site of infection (39). Neutralizing antibodies to adenylate cyclase toxin promote phagocytosis of *Bordetella pertussis* by human neutrophils (40). Immunization with AC-Hly, or AC could prevent colonization of the lungs, and reduce asymptomatic carriage, not only of *B. pertussis*, but also of other *Bordetella* pathogens for humans. Adenylate cyclase (AC) toxin from *Bordetella pertussis* is a 177-kDa repeats-in-toxin (RTX) family protein that consists of four principal domains; the catalytic domain, the hydrophobic domain, the glycine/aspartate rich repeat domain, and the secretion signal domain (41). The AC toxin of *B. pertussis* can be produced as a genetically detoxified recombinant form in *E. coli*. These recombinant toxins can be produced among others, in the *E. coli* strain BL (Novagen, Madison, Wis.) by using expression vectors that are derivatives of the pTRACG plasmid (42).

In a preferred embodiment, the Pertussis vaccine formulation comprises a genetically detoxified recombinant pertussis toxin (rPT). Priming to PT, a major virulence factor present in all aP vaccines, could be misdirected due to chemical (specifically formaldehyde) detoxification processes used during production, which removes up to 80% of surface epitopes. Chemical detoxification reduces immunogenicity of PT and could lead to original antigenic sin i.e., utilization of immune memory to the PT vaccine epitopes to produce antibodies that are ineffective against a wild-type strain in response to subsequent doses/exposure (32-34).

In another preferred embodiment is directed to vaccines that comprise in addition to dPT a detoxified adenylate cyclase toxin (dACT). PT plays an important early role for *B. pertussis* infection by delaying the influx of neutrophils to the site of infection during the first 24 to 48 h post inoculation and that ACT then plays an important role in the intoxication of recruited neutrophils after the interaction of the bacteria with these cells. ACT is known to enter cells efficiently after binding to the CD11b/CD18 integrin receptor present on neutrophils and to have deleterious effects on neutrophil activities, and after a study on the closely related pathogen *Bordetella bronchiseptica*, neutrophils were identified as the major target cells for ACT in promoting infection. Therefore, these toxins may provide a one-two punch on neutrophil recruitment and activity that is essential for optimal infection and colonization of the respiratory tract by *B. pertussis*.

In another embodiment, the invention comprises a lipo oligosaccharide conjugate to generate bactericidal antibodies effective at producing a sterilizing immune response and reduce bacterial carriage and thus the incidence of disease. In another preferred embodiment the vaccine comprises a core oligosaccharide derived from the *B. pertussis* lipo oligosaccharide endotoxin having one or more of the antigenic determinants of the endotoxin conjugated to a carrier protein or peptide.

In another embodiment, the invention provide a Pertussis vaccine formulation comprising a Toll-like receptor (TLR), preferably a TLR4 or TLR2 agonist as an adjuvant to shift the immune response towards a Th1/Th17 cell response to mediate protective cellular immunity to *B. pertussis*. Evidence shows that genetically detoxified pertussis toxin (dPT)-induced Th17 expansion is counter regulated by the PI3K pathway. For its properties and being already used in humans as vaccine Ag in pertussis, dPT may represents a valid candidate adjuvant to foster immune protective response in vaccines against infectious diseases where Th1/Th17 are mediating host immunity (45).

The following examples illustrate embodiments of the invention, but should not be viewed as limiting the scope of the invention.

Example 1 Construction of cyaA Mutants

Figure 1:
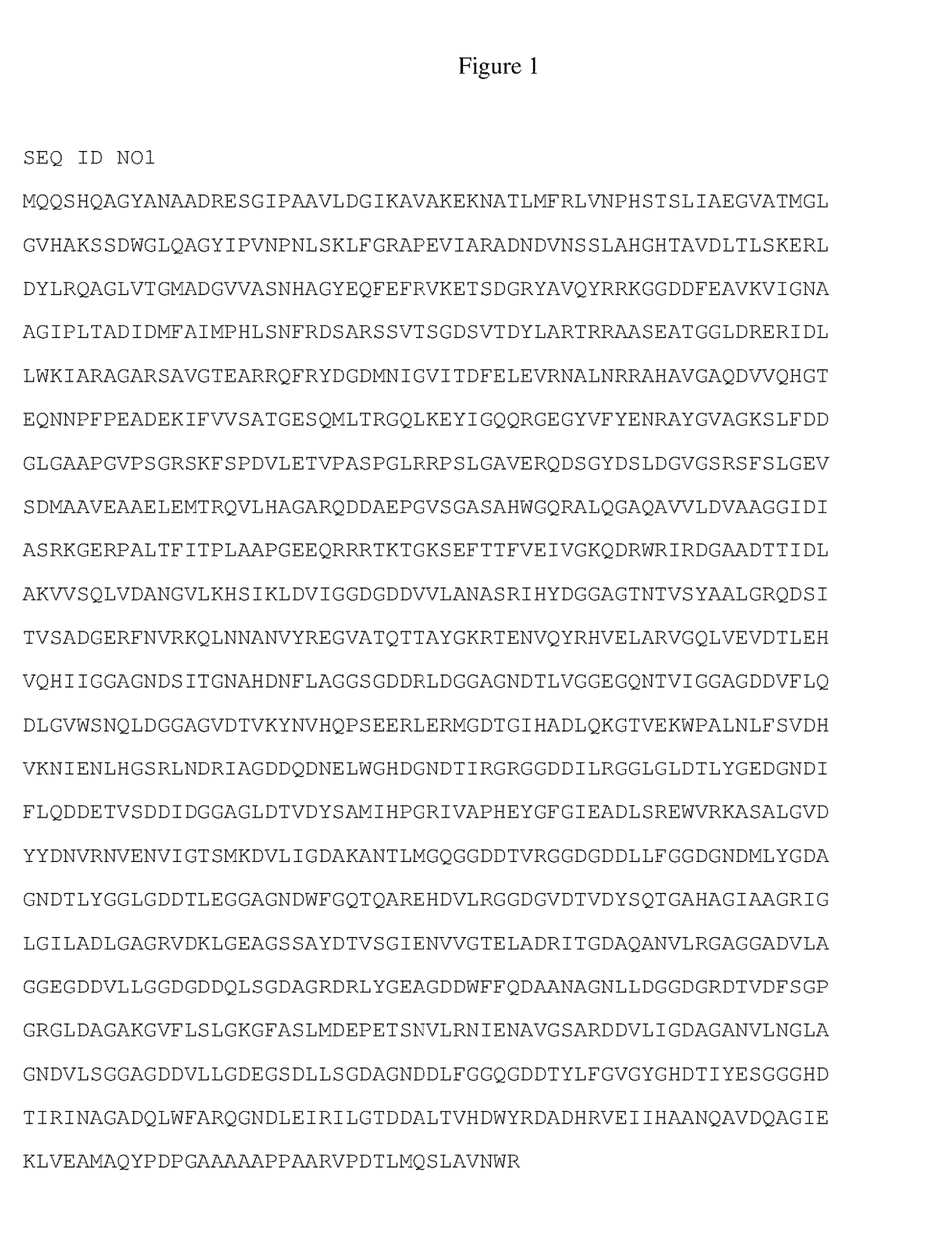
FIG. 1 depicts the Sequence ID No 1 amino acid sequence of a B. pertussis detoxified adenylate cyclase toxin.

Construction of cyaA mutants was performed on a 2.7-kilobase (kb) BamHI-EcoRI fragment of cyaA subcloned in pUC19 and expressed in E. coli (47). A mutant cyaA fragment carrying a selectable marker approximately equidistant between the two regions of cyaA to be specifically mutated was created by insertion of a 1.6-kb BamHI kanamycin-resistance cassette from pUC4-KIXX (Pharmacia) into the Bcl I site of cyaA. Oligonucleotide-directed mutagenesis to substitute methionine for lysine at position 58 of cyaA was performed as described (47) to produce the mutant cyaA fragment used for the creation of the AC-point mutant strain A2-6. Excision of a 1047-base-pair pflMI fragment of cyaA and religation produced the mutant cyaA fragment used for the creation of the HLY-deletion mutant strain 32-5 which lacks amino acids 469-817 of the cyaA toxin. All of the mutant cyaA fragments were subsequently excised from pUC19 and ligated in the appropriate orientation into a recombinant pSS1129 vector carrying an additional 2-kb BamHI fragment from directly upstream of cyaA. Mutant strains of B. pertussis were created by conjugative transfer of these recombinant pSS1129 vectors and selection for genetic recombination, according to the method of Stibitz et al. (48). Allelic exchange of the AC- or HLY-mutant cyaA gene was accomplished in a two-step process to ensure that genetic recombination did not occur outside cyaA. The chromosomal cyaA was first marked with a selectable phenotype by homologous recombination of the kanamycin resistance insertion mutation into B. pertussis, creating AC- and HLY-strains (S7c2). In the second cycle, the marked chromosomal gene was replaced with either the ACpoint mutation or the HLY-deletion mutation; recombination at the appropriate site was confirmed by phenotype analysis and either Southern (49) or immunologic blot analysis. The amino acid sequence of a detoxified CyaA variant sequence of Bordetella pertussis is shown in FIG. 1.

Example 2 Construction of Oligosaccharide Conjugates

Oligosaccharide conjugates of B. pertussis endotoxin and bronchiseptica induce bactericidal antibodies, an addition to pertussis vaccine, such conjugates are easy to prepare and standardize; added to a recombinant pertussis toxoid, they may induce antibacterial and antitoxin immunity(20, 46). The endotoxin core oligosaccharide can be obtained from the B. bronchiseptica RB50 LPS core OS structure which is similar to that of B. pertussis Tohama I and Tax 113, with an additional component, an O-SP. The dodecasaccharide core of B. bronchiseptica RB50 (FIG. 2A) without its O-SP (commonly referred to as "band A") can easily be separated on a Bio-Gel P-4 column, activated and conjugated to carrier protein. B. bronchiseptica is also a logical production strain to obtain the endotoxin core oligosaccharide because it is easier to grow than B. pertussis.

Example 3 Construction of the Pentasaccharide

The pentasaccharide part of the conjugate is a fragment isolated from the LOS of B. pertussis 186 and comprises distal trisaccharide, heptose and anhydromannose. Pentasaccharide-TTd conjugate can induce antibodies which were able to bind to B. pertussis in immunofluorescence assays (FACS). The terminal pentasaccharide of the lipooligosaccharide from B. pertussis strain 186 can be generated after extraction of bacterial cells by the hot phenolwater method and purified by ultracentrifugation (51). The pentasaccharide can be selectively cleaved from the LOS by treatment with nitrous acid. Briefly, the lipooligosaccharide (50 mg) was suspended in a freshly prepared solution (180 ml) containing water, 5% sodium nitrite, and 30% acetic acid (1:1:1, vol/vol/vol) and incubated for 4 h at 25° C., and this was followed by ultracentrifugation (200,000 g, 2 h). The supernatant was freeze-dried, and the product was purified on a column of Bio-Gel P-2 (Bio-Rad), yielding 10 mg of pentasaccharide which structure is shown in FIG. 2 (Formula 2), and analyzed by MALDI-TOF MS and NMR spectroscopy.

Example 4 Forming a Immunogenic Oligosaccharide-Protein Conjugate

Figure 2:
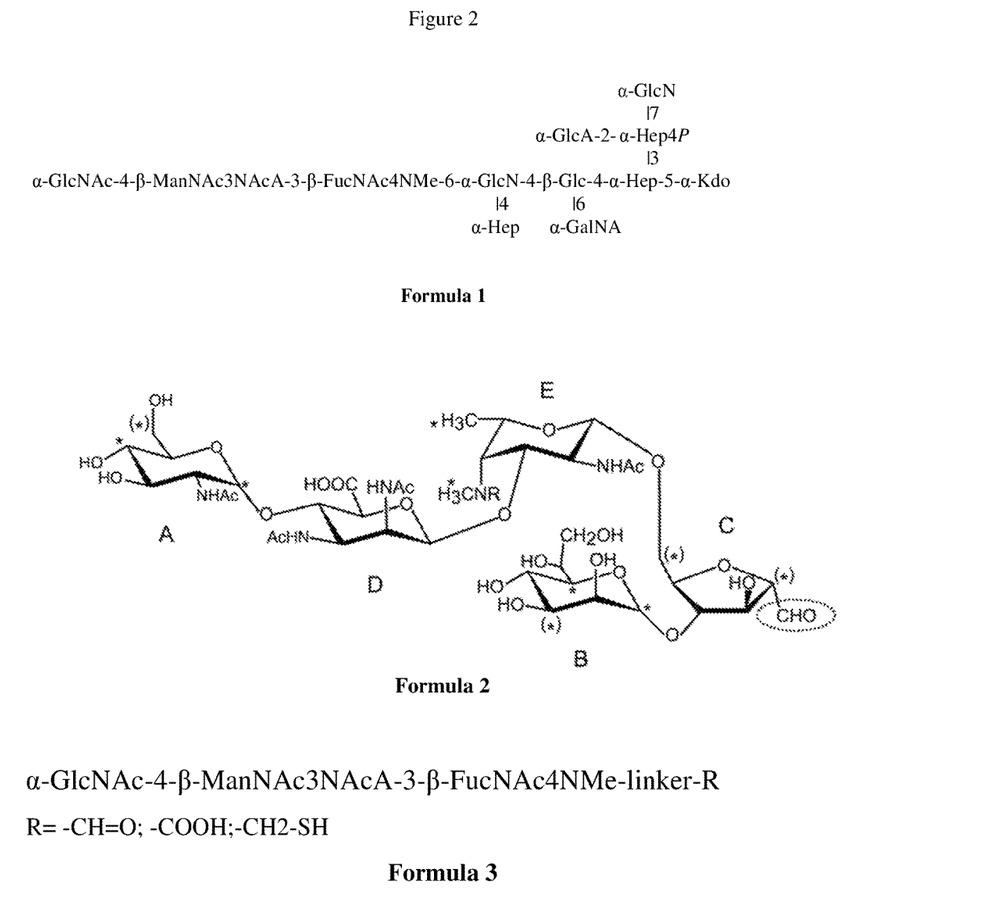

Synthetic trisaccharide (distal trisaccharide residues A, D, E) of structure shown in FIG. 2 (Formula 3) equipped with a spacer linker with a terminal aldehyde or other appropriate functional group were prepared with a conjugate immunogen to raise an antibody against such trisaccharide that would interact with B. pertussis LOS in vivo and promote agglutination, phagocytosis, and bacterial killing, as well as neutralizing the endotoxic activity of the LOS.

Formation of an immunogenic oligosaccharide-protein conjugate either or each of the dodecasaccharide (FIG. 2) or pentasaccharide or terminal trisaccharide (FIG. 2) is coupled to protein carriers by direct coupling of the reducing end KDO residue, or 2,5 anhydromannose of the pentasaccharide by reductive amination (with or without a linker) and condensation with primary amino groups of the carrier protein. Alternatively, the immunogenic conjugates of the invention may be prepared by direct coupling of the oligosaccharide by treatment with a carbodiimide forming a carboxylate intermediate which readily condenses with primary amino groups of the carrier protein. Preferred carrier proteins include, but are not limited to, CRMs, tetanus toxoid, diphtheria toxoid, cholera toxin subunit B, Neisseria meningitidis outer membrane proteins, pneumolysoid, C-β protein from group B Streptococcus, non-IgA binding C-β protein from group B Streptococcus, Pseudomonas aeruginosa toxoid, pertussis toxoid, synthetic protein containing lysine or cysteine residues, and the like. The carrier protein may be a native protein, a chemically modified protein, a detoxified protein or a recombinant protein. Conjugate molecules prepared according to this invention, with respect to the protein component, may be monomers, dimers, trimers and more highly cross-linked molecules.

Other embodiments and uses of the invention will be apparent to those skilled in the art from consideration of the specification and practice of the invention disclosed herein. All references cited herein, including all publications, and all U.S. and foreign patents and patent applications are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

REFERENCES

1. Preston A, Maskell D J. (2002) A new era of research into *Bordetella pertussis* pathogenesis. J Infect. 44:13-6.
2. Poland G A. (2012) Pertussis outbreaks and pertussis vaccines: new insights, new concerns, new recommendations? Vaccine. 30:6957-9
3. Fisman D N, et al. (2011) Pertussis resurgence in Toronto, Canada: a population-based study including test-incidence feedback modeling. BMC Public Health. 11:694
4. Hong J Y. (2010) Update on pertussis and pertussis immunization. Korean J Pediatr. 53:629-33
5. Rohani P, Zhong X, King A A. (2010) Contact network structure explains the changing epidemiology of pertussis. Science. 330:982-5.
6. Witt M A, Katz P H, Witt D J. (2012) Unexpectedly limited durability of immunity following acellular pertussis vaccination in preadolescents in a North American outbreak. Clin Infect Dis. 54:1730-5.
7. Witt M A, Arias L, Katz P H, Truong E T, Witt D J. (2013) Reduced risk of pertussis among persons ever vaccinated with whole cell pertussis vaccine compared to recipients of acellular pertussis vaccines in a large US cohort. Clin Infect Dis. 56:1248-54.
8. Clark T A, Bobo N. (2012) CDC update on pertussis surveillance and Tdap vaccine recommendations. NASN Sch Nurse. 27:297-300.
9. de Greeff S C, et al. (2010) Pertussis disease burden in the household: how to protect young infants. Clin Infect Dis.; 50:1339-45.
10. Paddock C D, et al. (2008) Pathology and pathogenesis of fatal *Bordetella pertussis* infection in infants. Clin Infect Dis. 47:328-38.
11. Melvin J, et al., (2014) *Bordetella pertussis* pathogenesis: current and future challenges. Nat Rev Microbiol. April; 12(4): 274-288.
12. Rappuoli R (1999) The vaccine containing recombinant pertussis toxin induces early and long-lasting immunity. Biologicals 27(2): 98-102.
13. Robbins J B, et al. (2007) The rise in pertussis cases urges replacement of chemically-inactivated with genetically-inactivated toxoid for DTP. Vaccine 25(15):2811-2816.
14. Taranger J, et al. (2001) Mass vaccination of children with pertussis toxoid—decreased incidence in both vaccinated and nonvaccinated persons. Clin Infect Dis 33(7): 1004-1010.
15. Le T, et al.; APERT Study (2004) Immune responses and antibody decay after immunization of adolescents and adults with an acellular pertussis vaccine: The APERT Study. J Infect Dis 190(3):535-544.
16. Trollfors B, Dotevall L, Sundh V, Welinder-Olsson C (2011) Pertussis after end of a mass vaccination project—End of the "vaccination honey-moon" Vaccine 29(13): 2444-2450.
17. Heininger U, Cherry J D, Stehr K (2004) Serologic response and antibody-titer decay in adults with pertussis. Clin Infect Dis 38(4): 591-594.
18. Linneman C C, Jr., Ramundo N, Perlstein P H, Minton D, Englander G S (1977) Use of pertussis vaccine in an epidemic involving hospital staff. Lancet 2:540-543.
19. Weiss A A, et al. (2004) Acellular pertussis vaccines and complement killing of *Bordetella pertussis*. Infect Immun 72(12): 7346-7351.
20. Kubler-Kielba J et al., (2011) Oligosaccharide conjugates of *Bordetella pertussis* and *bronchiseptica* induce bactericidal antibodies, an addition to pertussis vaccine. Proc Natl Acad Sci USA vol. 108:4089.
21. Eby J C, Gray M C, Warfel J M, et al. (2013) Quantification of the adenylate cyclase toxin of *Bordetella pertussis* in vitro and during respiratory infection. Infect Immun 81:1390-8.
22. Robbins J B, Schneerson R, Kubler-Kielb J, et al. (2014) Toward a new vaccine for pertussis. Proc Natl Acad Sci USA 111:3213-16.
23. Cherry J D et al., (2004) "Determination of serum antibody to *Bordetella pertussis* anenylate cyclase toxin in vaccinated and unvaccinated children and in children and adults with pertussis," Clinical Infectious Diseases, vol. 15, no. 4, pp. 502-5073
24. Dunne A et al., (2014) A novel TLR2 agonist from *Bordetella pertussis* is a potent adjuvant that promotes protective immunity with an acellular pertussis vaccine. Mucosal Immunology 10/2014; DOI: 10.1038/mi.2014.93
25. Ryan M, Murphy G, Ryan E, Nilsson L, Shackley F, et al. (1998) Distinct T-cell subtypes induced with whole cell and acellular pertussis vaccines in children. Immunology 93: 1-10.
26. Ausiello C M, Urbani F, la Sala A, Lande R, Cassone A (1997) Vaccine- and antigen-dependent type 1 and type 2 cytokine induction after primary vaccination of infants with whole-cell or acellular pertussis vaccines. Infect Immun 65: 2168-2174.
27. Mahon B P, Brady M T, Mills K H (2000) Protection against *Bordetella pertussis* in mice in the absence of detectable circulating antibody: implications for longterm immunity in children. J Infect Dis 181: 2087-2091.
28. Higgins S C, Jarnicki A G, Lavelle E C, Mills K H (2006) TLR4 mediates vaccine-induced protective cellular immunity to *Bordetella pertussis*: role of IL-17 producing T cells. J Immunol 177: 7980-7989.
29. Dunne A, Ross P J, Pospisilova E, Masin J, Meaney A, et al. (2010) Inflammasome activation by adenylate cyclase toxin directs Th17 responses and protection against *Bordetella pertussis*. J Immunol 185: 1711-1719.
30. Fedele G, Spensieri F, Palazzo R, Nasso M, Cheung G Y, et al. (2010) *Bordetella pertussis* commits human dendritic cells to promote a Th1/Th17 response through the activity of adenylate cyclase toxin and MAPK-pathways. PLoS One 5: e8734.
31. Andreasen C, Powell D A, Carbonetti N H (2009) Pertussis toxin stimulates IL-17 production in response to *Bordetella pertussis* infection in mice. PLoS One 4: e7079.
32. Ibsen P H (1996) The effect of formaldehyde, hydrogen peroxide and genetic detoxification of pertussis toxin on epitope recognition by murine monoclonal antibodies. Vaccine 14:359-68.
33. Francis T., "On the doctrine of original antigenic sin," Proceedings of the American Philosophical Society, vol. 104, no. 6 (Dec. 15, 1960), pp. 572-578.
34. Lavine J S, King A A, Bjørnstad O N. (2011) Natural immune boosting in pertussis dynamics and the potential for long-term vaccine failure. Proc Natl Acad Sci USA. April 26; 108(17):7259

35. Vojtova J, Kamanova J, Sebo P. (2006) *Bordetella* adenylate cyclase toxin: a swift saboteur of host defense. Curr Opin Microbiol 9:69-75.
36. Goodwin M S, Weiss A A. (1990) Adenylate cyclase toxin is critical for colonization and pertussis toxin is critical for lethal infection by *Bordetella pertussis* in infant mice. Infect Immun 58:3445-3447.
37. Gross M K, Au D C, Smith A L, Storm D R. (1992) Targeted mutations that ablate either the adenylate cyclase or hemolysin function of the bifunctional cyaA toxin of *Bordetella pertussis* abolish virulence. Proc Natl Acad Sci USA 89:4898-4902.
38. Khelef N, Sakamoto H, Guiso N. (1992) Both adenylate cyclase and hemolytic activities are required by *Bordetella pertussis* to initiate infection. Microb Pathog 12:227-235.
39. Carbonetti N H, Artamonova G V, Andreasen C, Bushar N. (2005) Pertussis toxin and adenylate cyclase toxin provide a one-two punch for establishment of *Bordetella pertussis* infection of the respiratory tract. Infect Immun 2005; 73:2698-2703.
40. Weingart C L, Mobberley-Schuman P S, Hewlett E L, Gray M C, Weiss A A. Neutralizing antibodies to adenylate cyclase toxin promote phagocytosis of *Bordetella pertussis* by human neutrophils. Infect Immun 2000; 68:7152-7155
41. Lee S J et al. (1999) Epitope mapping of monoclonal antibodies against *Bordetella pertussis* adenylate cyclase toxin. Infect Immun. 67(5):2090-5.
42. Gmira, S., Karimova, G. and Ladant, D. (2001) Characterization of recombinant *Bordetella pertussis* adenylate cyclase toxins carrying passenger proteins. Res. Microbiol. 152:889.
43. Pizza M, Covacci A, Bartoloni A, et al. (1999) Mutants of pertussis toxin suitable for vaccine development. Science 246:497-500
44a. Nencioni, L., G. Volpini, S. Peppoloni, M. Bugnoli, T. De Magistris, I. Marsili, and R. Rappuoli. (1991) Properties of pertussis toxin mutant PT-9K/129G after formaldehyde treatment. Infect. Immun. 59: 625-630
44b. Nencioni, L, Pizza, M., Bugnoli, M., De Magistris, T., Di Tommaso, A Giovannoni, R, Manetti, R. Marsili, I., Matteucci, G., and Nucci. D. (1990). Characterization of genetically inactivated pertussis toxin mutants: candidates for a new vaccine against whooping cough. Infect Immun 58, 1308-1315.
45. Nasso M et al. (2009) Genetically Detoxified Pertussis Toxin Induces Th1/Th17 Immune Response through MAPKs and IL-10-Dependent Mechanisms. J Immunol, 183:1892-1899.
46. Kimura A et al., (1991) European Patent Application 0471954A2 immunogenic conjugates of non toxic oligosaccharides derived from *B. pertussis* lipooligosaccharide
47. Au, D. C., Masure, H. R. & Storm, D. R. (1989) Biochemistry 28, 2772-2776.
48. Stibitz, S., Black, W. & Falkow, S. (1986) Gene 50, 133-140.
49. Southern, E. M. (1975) J. Mol. Biol. 98, 503-517.
50. Guiso N, Szatanik M, Rocancourt M. Protective activity of *Bordetella* adenylate cyclase-hemolysin against bacterial colonization. Microb Pathog 1991; 11:423-431.
51. Niedziela, T et al. Epitope of the Vaccine-Type *Bordetella pertussis* Strain 186 Lipooligosaccharide and Anti-endotoxin Activity of Antibodies Directed against the Terminal Pentasaccharide-Tetanus Toxoid Conjugate. Infect Immun 2005, 73:7381-7389.
52. Caroff, M., Chaby, R., Karibian, D., Perry, J., Deprun, C, and Szabo, L. (1990). Variations in the carbohydrate regions of *Bordetella pertussis* lipopolysaccharides: electrophoretic, serological, and structural features. J Bacteriol 172, 1121-1128.
53. Caroff, M., Brisson, J., Martin, A., and Karibian, D. (2000). Structure of the *Bordetella pertussis* 1414 endotoxin. FEBS Lett. 477, 8-14.

The invention claimed is:

1. An immunogenic *B. pertussis* vaccine composition comprising a genetically detoxified pertussis toxin (PT); a genetically detoxified pertussis adenylate cyclase toxin (ACT) containing the amino acid sequence of SEQ ID NO 1; an immunogenic oligosaccharide or fragment thereof derived from the lipooligosaccharide of *B. pertussis* having one or more of the antigenic determinants of the endotoxin to a carrier protein or peptide; a TLR agonist to induce a protective cell-mediated response against *B. pertussis* wherein when provided to a mammal said composition:
- produces neutralizing anti toxin antibodies against *B. pertussis*;
- produces direct bactericidal antibodies against *B. pertussis*;
- elicits a pertussis toxin-specific Th1/Th17 cell response;

generates IFN-δ and IL-17 cytokines wherein said cytokines permit recruitment of neutrophils; and reduces nasopharyngeal colonization and carriage of *B. pertussis* in the vaccine recipient.

2. The vaccine of claim 1, wherein the genetically detoxified pertussis toxin is produced in *E. coli, B. pertussis* or *B. bronchiseptica.*

3. The vaccine of claim 1, wherein the genetically detoxified pertussis toxin comprises a mutation of pertussis toxin that is produced in *B. pertussis, B. bronchiseptica* or *E. coli.*

4. The vaccine of claim 1, wherein the genetically detoxified AC toxin is produced in *E. coli, B. pertussis* or *B. bronchiseptica.*

5. The vaccine of claim 1, which induces the production of anti-PT and anti-ACT neutralizing and bactericidal antibodies against *B. pertussis.*

6. An oligosaccharide conjugate comprising a genetically detoxified pertussis toxin (PT); a genetically detoxified pertussis adenylate cyclase toxin (ACT) containing the amino acid sequence of SEQ ID NO 1; an immunogenic oligosaccharide or fragment thereof derived from the lipooligosaccharide of *B. pertussis* having one or more of the antigenic determinants of the endotoxin to a carrier protein or peptide; a TLR agonist to induce a protective cell-mediated response against *B. pertussis.*

7. The conjugate of claim 6, wherein the oligosaccharide is selected from the group consisting of the structure of the dodecasaccharide core of *B. bronseptica* LOS, the structure of the pentasaccharide hapten obtained by deamination of the LOS of *B. pertussis* strain 186, and the structure of a synthetic *B. pertussis* epitope distal LOS trisaccharide with a spacer and a terminal aldehyde.

8. The conjugate of claim 7, wherein the structure of the synthetic *B. pertussis* epitope distal LOS trisaccharide with a spacer and a terminal aldehyde is synthetic or a deamination product of the *B. pertussis* LOS.

9. The conjugate of claim 6, wherein the oligosaccharide comprises a *B. pertussis* LOS-derived oligosaccharide (OS) or a fragment thereof, and the *B. pertussis* derived detoxified toxin (dPT).

10. The conjugate of claim 6, wherein the oligosaccharide comprises a *B. pertussis* LOS-derived oligosaccharide (OS) or its fragment and the pertussis derived detoxified toxin (dACT).

11. The conjugate of claim 6, wherein the TLR agonist is a TLR-2, a TLR-4 or a TLR-8.

12. An oligosaccharide conjugate comprising a genetically detoxified pertussis toxin (PT); a genetically detoxified pertussis adenylate cyclase toxin (ACT); an immunogenic oligosaccharide or fragment thereof derived from the lipooligosaccharide of *B. pertussis* having one or more of the antigenic determinants of the endotoxin to a carrier protein or peptide; a TLR agonist to induce a protective cell-mediated response against *B. pertussis*, wherein the oligosaccharide comprises one or more of the oligosaccharides of the structure of the dodecasaccharide core of *B. bronseptica* LOS, the structure of the pentasaccharide hapten obtained by deamination of the LOS of *B. pertussis* strain 186, or the structure of a synthetic *B. pertussis* epitope distal LOS trisaccharide comprising a spacer and a terminal aldehyde.

13. The conjugate of claim 12, wherein the genetically detoxified pertussis adenylate cyclase toxin (ACT) comprises the amino acid sequence of SEQ ID NO 1.

14. The conjugate of claim 12, wherein the structure of the synthetic *B. pertussis* epitope distal LOS trisaccharide comprises a spacer and a terminal aldehyde.

15. The conjugate of claim 14, wherein the synthetic *B. pertussis* epitope distal LOS trisaccharide is a deamination product of the *B. pertussis* LOS.

16. The conjugate of claim 12, wherein the oligosaccharide comprises a *B. pertussis* LOS-derived oligosaccharide (OS) or its fragment and the *B. pertussis* derived detoxified toxin (dPT).

17. The conjugate of claim 12, wherein the oligosaccharide comprises a *B. pertussis* LOS-derived oligosaccharide (OS), or a fragment thereof, and the pertussis derived detoxified toxin (dACT).

18. The conjugate of claim 12, wherein the TLR agonist is a TLR-2, a TLR-4 or a TLR-8.

19. The conjugate of claim 12, wherein the genetically detoxified pertussis toxin is produced in *E. coli, B. pertussis* or *B. bronchiseptica.*

20. The conjugate of claim 12, wherein the genetically detoxified pertussis toxin comprises a mutation of pertussis toxin that is produced in *B. pertussis, B. bronchiseptica* or *E. coli.*

21. The conjugate of claim 12, wherein the genetically detoxified AC toxin is produced in *E. coli, B. pertussis* or *B. bronchiseptica.*

22. A vaccine comprising the oligosaccharide conjugate of claim 6.

23. A vaccine comprising the oligosaccharide conjugate of claim 12.

* * * * *

UNITED STATES PATENT AND TRADEMARK OFFICE
CERTIFICATE OF CORRECTION

PATENT NO. : 10,076,563 B2
APPLICATION NO. : 15/131674
DATED : September 18, 2018
INVENTOR(S) : Subhash V. Kapre and Francis Michon Page 1 of 1

It is certified that error appears in the above-identified patent and that said Letters Patent is hereby corrected as shown below:

In Claim 1, on Line 14, please delete "of the antigenic determinants of the endotoxin" and insert therefore --antigenic determinants, conjugated--
In Claim 1, on Line 15, before "a TLR agonist" please insert --and--
In Claim 1, on Line 18, please delete "anti toxin" and insert therefore --anti-toxin--
In Claim 6, on Lines 44-45, please delete "of the antigenic determinants of the endotoxin" and insert therefore --antigenic determinants, conjugated--
In Claim 6, on Line 46, before "a TLR agonist" please insert --and--
In Claim 12, on Lines 17-18, please delete "of the antigenic determinants of the endotoxin" and insert therefore --antigenic determinants, conjugated--
In Claim 12, on Line 19, before "a TLR agonist" please insert --and--

Signed and Sealed this
Twenty-third Day of October, 2018

Andrei Iancu
*Director of the United States Patent and Trademark Office*